(12) United States Patent
Kadaba et al.

(10) Patent No.: US 12,011,370 B2
(45) Date of Patent: Jun. 18, 2024

(54) EXPANDABLE VERTEBRAL SPACER WITH FOUR LOCKING MECHANISMS

(71) Applicant: Ingeniumspine, LLC, Phoenix, AZ (US)

(72) Inventors: Murali Kadaba, Austin, TX (US); Damien Shulock, San Francisco, CA (US); B. Thomas Barker, Bartlett, TN (US); Dennis Crandall, Mesa, AZ (US); Jason Datta, Phoenix, AZ (US); Lyle Young, Phoenix, AZ (US)

(73) Assignee: Ingeniumspine, LLC, Phoenix, AZ (US)

( * ) Notice: Subject to any disclaimer, the term of this patent is extended or adjusted under 35 U.S.C. 154(b) by 0 days.

(21) Appl. No.: 18/215,072

(22) Filed: Jun. 27, 2023

(65) Prior Publication Data
US 2024/0000583 A1  Jan. 4, 2024

Related U.S. Application Data

(60) Provisional application No. 63/357,411, filed on Jun. 30, 2022.

(51) Int. Cl.
*A61F 2/44* (2006.01)
*A61F 2/46* (2006.01)
*A61F 2/30* (2006.01)

(52) U.S. Cl.
CPC .......... *A61F 2/447* (2013.01); *A61F 2/4611* (2013.01); *A61F 2002/30494* (2013.01); *A61F 2002/30505* (2013.01); *A61F 2002/30556* (2013.01); *A61F 2002/30579* (2013.01); *A61F 2002/4692* (2013.01)

(58) Field of Classification Search
CPC .......... A61F 2/447; A61F 2/44; A61F 2/4611; A61F 2002/30494; A61F 2002/30505; A61F 2002/30556; A61F 2002/30579; A61F 2002/4692
USPC .......................................... 623/17.11–17.16
See application file for complete search history.

(56) References Cited

U.S. PATENT DOCUMENTS

| | | | | |
|---|---|---|---|---|
| 6,159,244 A | * | 12/2000 | Suddaby | A61F 2/4611 606/247 |
| 6,562,074 B2 | * | 5/2003 | Gerbec | A61F 2/4611 623/17.15 |
| 8,828,085 B1 | * | 9/2014 | Jensen | A61F 2/447 623/17.11 |

(Continued)

*Primary Examiner* — Jessica Weiss
(74) *Attorney, Agent, or Firm* — Etherton Law Group, LLC

(57) ABSTRACT

Expandable intervertebral spacer system having a top plate and a bottom plate which are separated and held apart a changeable distance forming a cage. The plates are held apart by four locking mechanisms in the cage at or near the corners or the periphery of the plates, leaving the cavity of the cage substantially unobstructed. Each locking mechanism is made of two saw-toothed posts that cooperate to lock the top plate a desired distance from the bottom plate. The saw-tooth posts are biased against each other with a spring. Once the spacer is implanted in a patient with a removable insertion tool, the top and bottom plates are forced apart incrementally, one saw tooth at a time, in a ratchet-like motion, using a removable expansion mechanism. Optionally, each stanchion is surrounded by a sheath to prevent bone particles and other debris from interfering with the mating of the saw teeth.

30 Claims, 12 Drawing Sheets

(56) References Cited

U.S. PATENT DOCUMENTS

| | | | | |
|---|---|---|---|---|
| 9,364,344 B2* | 6/2016 | Whipple | ............... | A61F 2/4455 |
| 9,539,109 B2* | 1/2017 | Spangler | ............... | A61L 31/005 |
| 10,729,553 B2* | 8/2020 | Bell | ............... | A61F 2/4455 |
| 10,729,554 B2* | 8/2020 | Bootwala | ............... | A61F 2/4455 |
| 11,234,833 B2* | 2/2022 | Brotman | ............... | A61F 2/4455 |
| 11,737,892 B1* | 8/2023 | Kadaba | ............... | A61F 2/30771 |
| | | | | 623/17.16 |
| 2007/0123987 A1* | 5/2007 | Bernstein | ............... | A61F 2/44 |
| | | | | 623/17.11 |
| 2010/0137987 A1* | 6/2010 | Diao | ............... | A61B 17/8852 |
| | | | | 623/17.11 |
| 2014/0188225 A1* | 7/2014 | Dmuschewsky | ....... | A61F 2/442 |
| | | | | 623/17.16 |
| 2019/0053912 A1* | 2/2019 | Suddaby | ............... | A61F 2/447 |
| 2021/0030562 A1* | 2/2021 | Suddaby | ............... | A61F 2/447 |

\* cited by examiner

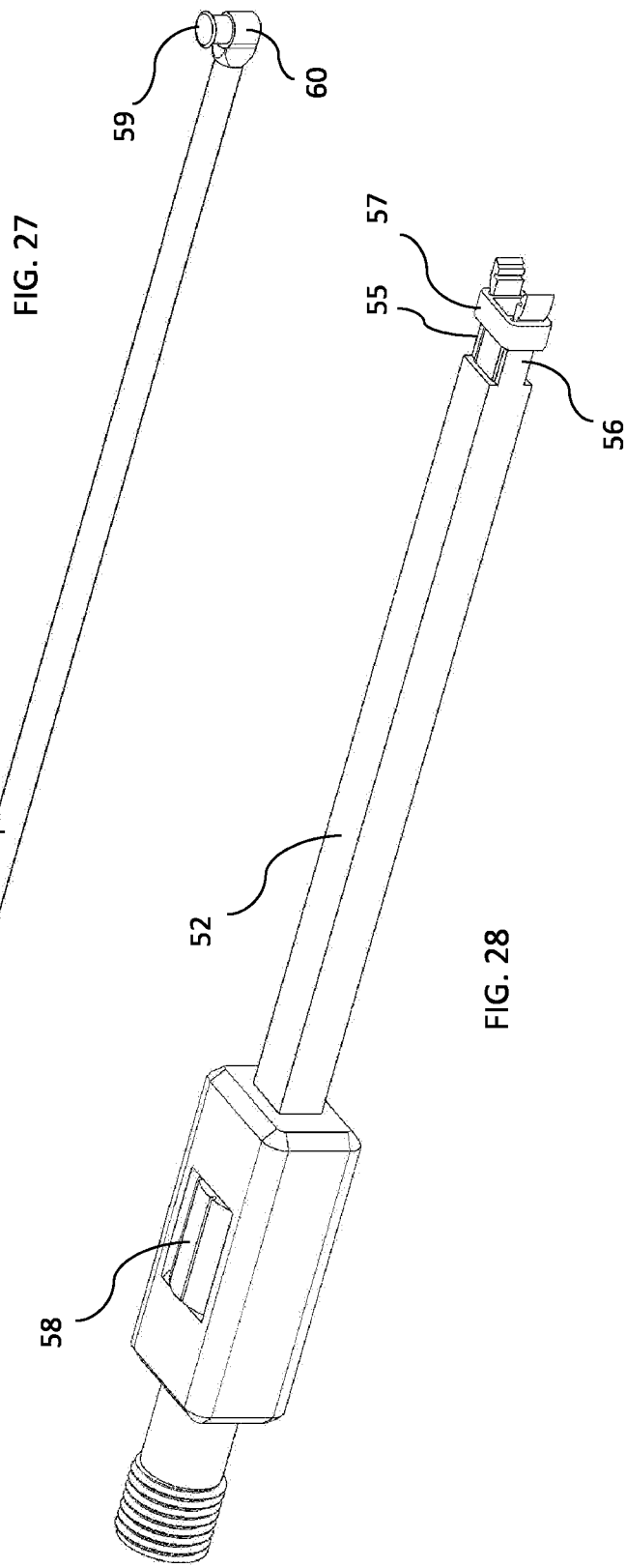
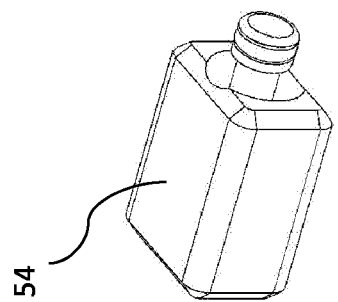
FIG. 27
FIG. 28

EXPANDABLE VERTEBRAL SPACER WITH FOUR LOCKING MECHANISMS

CROSS-REFERENCE TO RELATED APPLICATIONS

This application claims the benefit of U.S. Provisional Application No. 63/357,411 filed Jun. 30, 2022.

FIELD OF INVENTION

The present invention relates generally to devices for orthopedic surgery of the spine. The present invention relates particularly to implants placed within an intervertebral disc space that are capable of expanding vertically.

BACKGROUND

Interbody fusion is a type of spine surgery that removes all or part of a degenerated disc from between two adjacent vertebrae in a patient's back. Once the disk is removed, an expandable device is inserted into the disc space between the adjacent vertebrae to forcibly space the vertebrae apart and maintain intervertebral separation. Cancellous bone graft material is packed in and around the spacer to provide a scaffolding so that new bone can be formed. During healing the adjacent vertebra fuse into a single monolithic bone bridge. The more graft material used, and the more surface area it has touching the patient's bone, the more likely the fusion will be successful. Therefore it is advantageous for the inserted device to have a large, open cage structure to receive and expose the bone graft material.

The expandable spacer is expanded using an expansion mechanism placed within the cage structure, such as a jack, cam, or balloon, typically by use of a mated insertion tool. If the expansion mechanism is integral with the spacer and therefore not removable, the volume of the graft cavity is reduced. It would be desirable use a removable expansion mechanism to maximize the open volume of the cage structure.

Once expanded, the spacer is locked at the desired height. The locking mechanism must be strong enough to withstand the compressive forces between the vertebrae and the cage must be robust enough so that it does not collapse or otherwise fail during the patient's lifetime. Strength and durability are vitally important, but making a spacer needlessly robust detracts from the size of the cavity in the spacer for holding bone graft material. A balance is desired.

It is an object of this invention to provide an expandable interbody spacer with a robust locking mechanism, which also has a large open cage that maximizes the available volume and exposure of bone graft material. It is another object of this invention to structure the locking mechanism with a removable expansion mechanism so that the cage is unobstructed.

SUMMARY OF THE INVENTION

An expandable intervertebral spacer system has a top plate and a bottom plate which are separated and held apart a changeable distance forming a cage. The plates are held apart by four locking mechanisms in the cage at or near the corners or the periphery of the plates, leaving the cavity of the cage substantially unobstructed. Each locking mechanism is made of two saw-toothed posts that cooperate to lock the top plate a desired distance from the bottom plate. The saw-tooth posts are biased against each other with a spring.

Once the spacer is implanted in a patient with a removable insertion tool, the top and bottom plates are forced apart incrementally, one saw tooth at a time, in a ratchet-like motion, using a removable expansion mechanism. Optionally, each stanchion is surrounded by a sheath to prevent bone particles and other debris from interfering with the mating of the saw teeth.

BRIEF DESCRIPTION OF THE DRAWINGS

FIG. 27 is a partially exploded perspective view of the syringe of the insertion tool of FIG. 24.

FIG. 28 is a partial perspective view of the shaft of the insertion tool of FIG. 24.

DETAILED DESCRIPTION OF THE INVENTION

Figure 1:
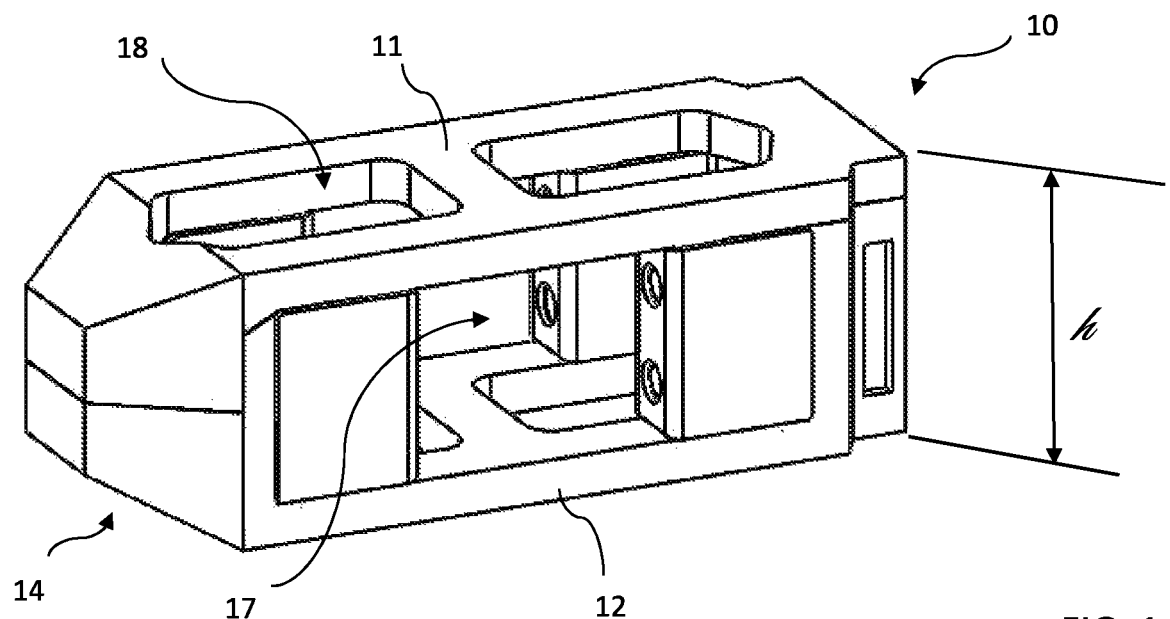
FIG. 1 is a top perspective view of a spacer in an unexpanded position.
Figure 2:
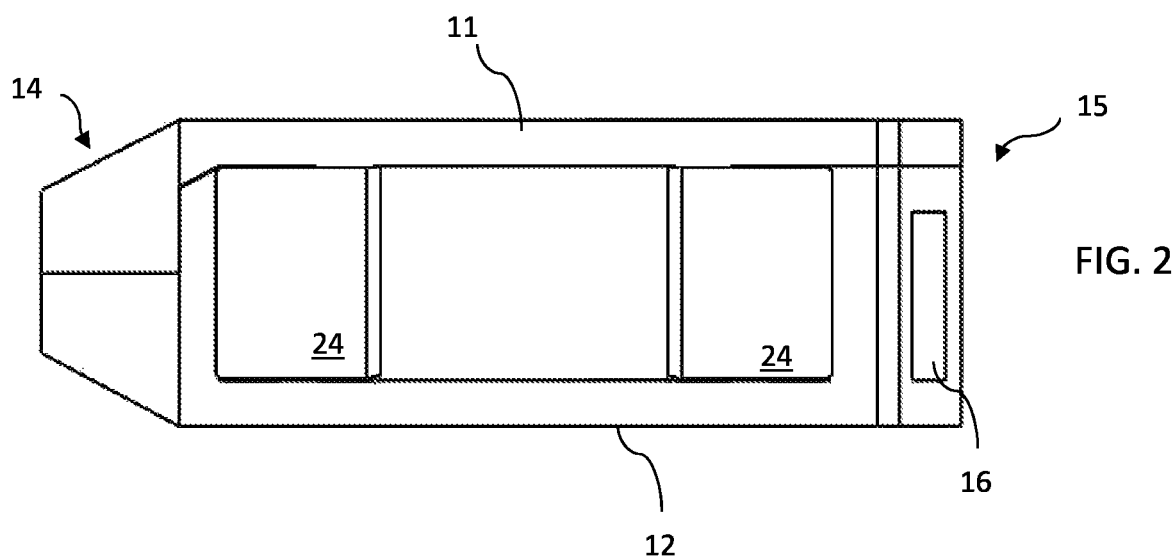
FIG. 2 is a side view of the spacer of FIG. 1 in an unexpanded position.
Figure 3:
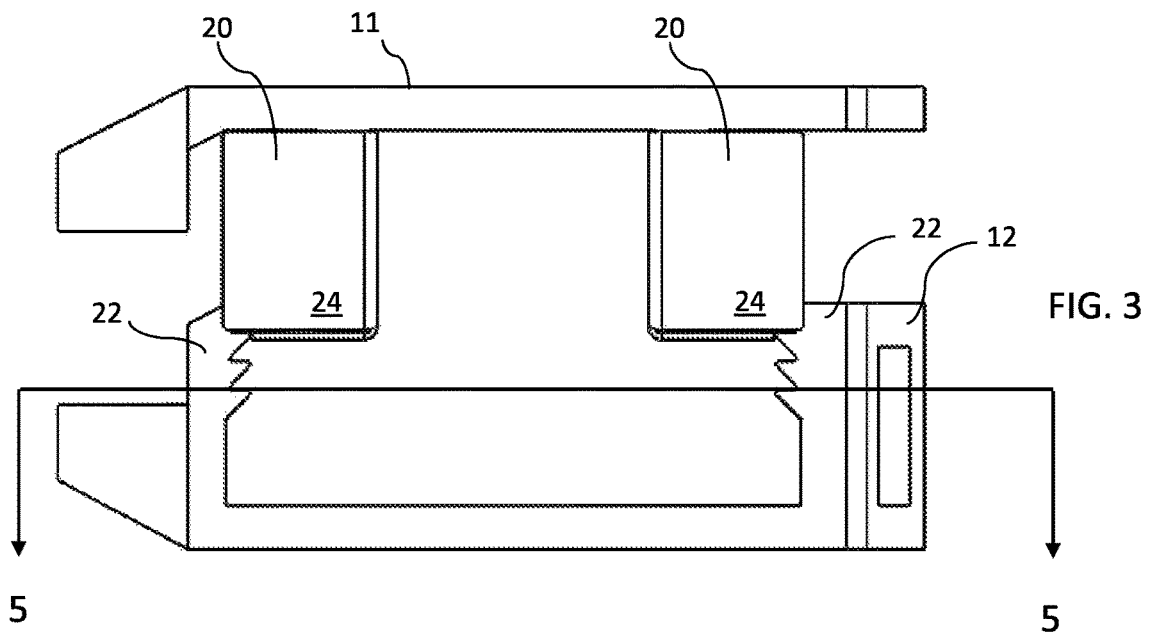
FIG. 3 is a side view of the spacer of FIG. 1 in an expanded position.
Figure 4:
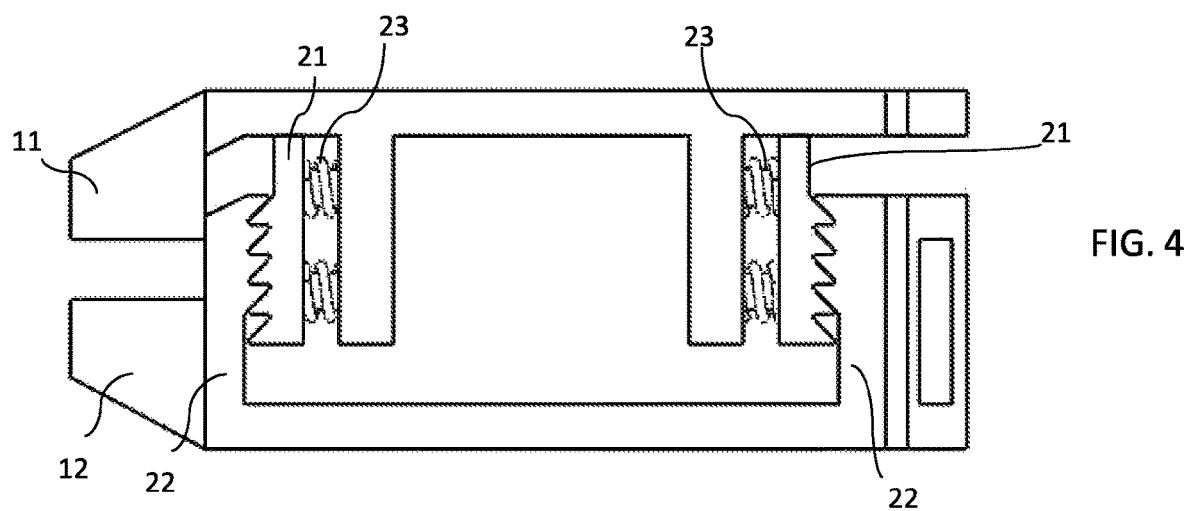
FIG. 4 is a side view of the spacer of FIG. 1 without the sheaths that cover the ratchet mechanisms, in a partially expanded position.

This expandable intervertebral spacer comprises a spacer body 10 comprising a top plate 11 and a bottom plate 12, and integral locking mechanisms that separate the plates and holds them apart at a desired distance. Each locking mechanism comprises a stanchion 20, each stanchion 20 comprising two saw-tooth posts that move relative to one another. To expand the spacer, the top and bottom plates are forced apart incrementally, one saw tooth at a time, in a ratchet-like motion using a removable expansion mechanism.

The top plate 11 and bottom plate 12 of the spacer body 10 cooperate to form an open-sided, substantially rectangular cage surrounding a cavity 17. The cage has a top, a bottom, two sidewalls, a distal end 14 and a proximal end 15. The portions of the plates forming the cage are generally shaped as squares or rectangles with rounded corners. See FIGS. 1-5 and 12-21. There are no flanges extending from the spacer body 10 away from the cavity, which were used in prior art devices for attaching the spacer to adjacent vertebrae, making the implantation of the box-like shape of the present invention less invasive than that of the prior art. Instead of continuous solid sheets of material, the cage has cutouts 18 to permit bone graft material to be more easily packed into the cavity 17 between the plates and increase the surface exposure of the graft material to the patient's vertebrae.

Figures 6, 7, 8:
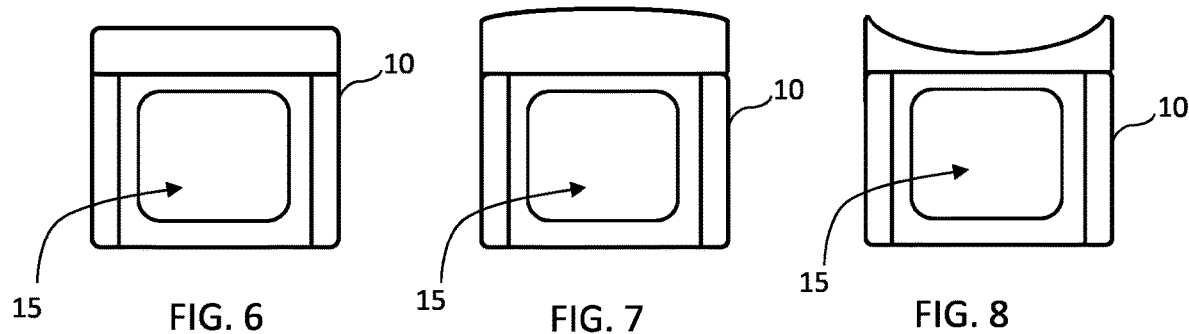
FIG. 6 is an end view of the spacer of FIG. 1 showing the opening for the insertion tool.
FIG. 7 is an end view of a first alternative embodiment of the spacer of FIG. 1 having a convex top, showing the opening for the insertion tool.
FIG. 8 is an end view of a second embodiment of the spacer of FIG. 1 having a concave top, showing the opening for the insertion tool.

Although the general shape of vertebrae are common between patients, the specific size, shape, lordosis, and condition of the cancellous bone are peculiar to each patient. These biological factors affect the size, shape and placement of the spacer. Each plate may be flat, concave or saddle-shaped, convex, or asymmetric, depending on the shape needed to most closely match the curvature of the surfaces of the patient's vertebrae. See FIGS. 6-8.

Figure 10:
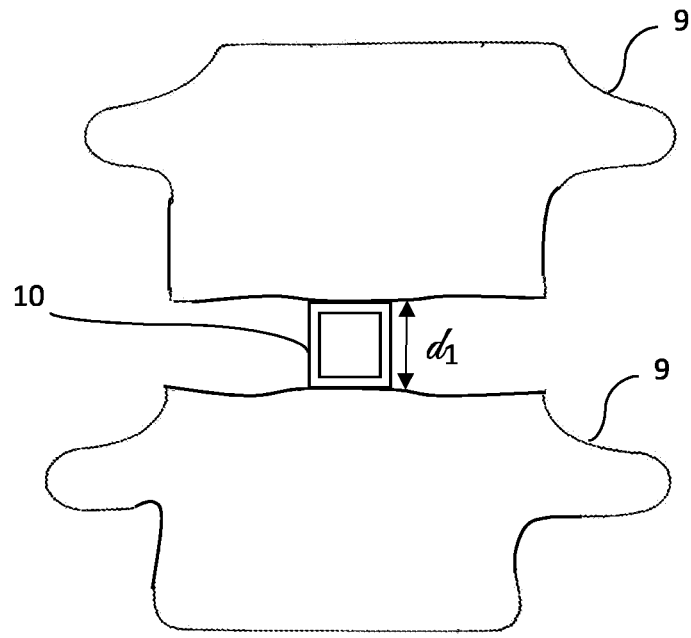
FIG. 10 is a schematic illustration of an unexpanded spacer between two vertebrae.
Figure 11:
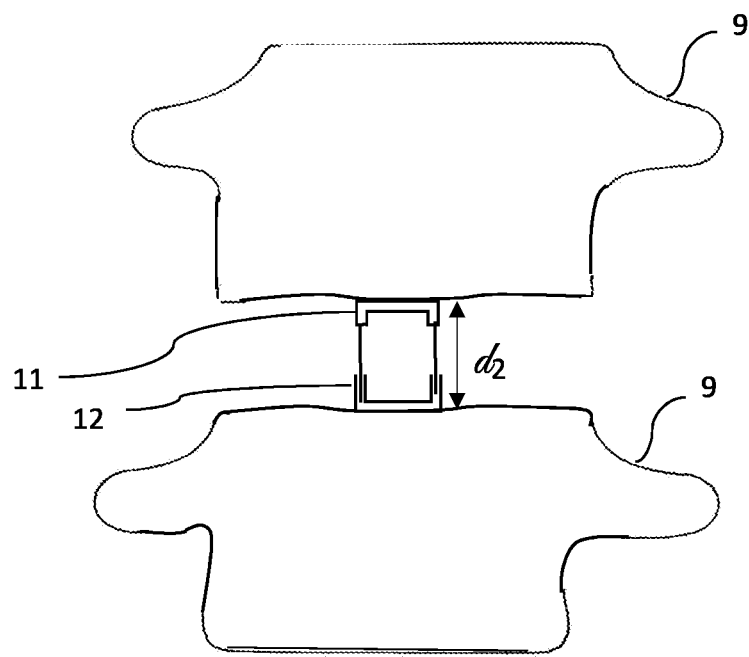
FIG. 11 is a schematic illustration of the spacer of FIG. 10 in an expanded state.
Figure 12:
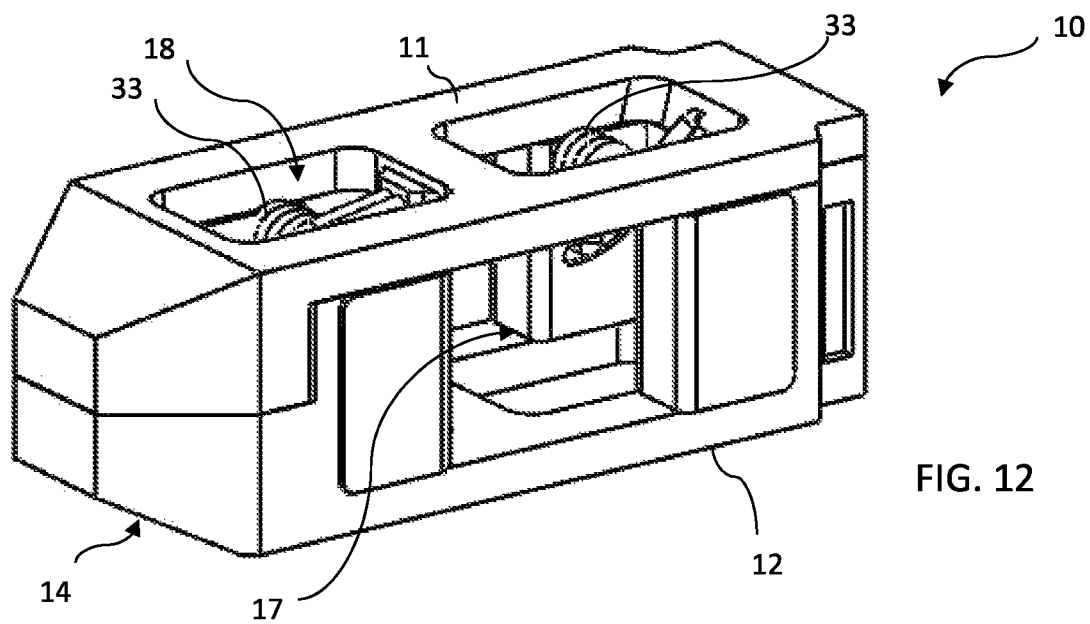
FIG. 12 is a top perspective view of a second embodiment of a spacer in an unexpanded position.
Figure 13:
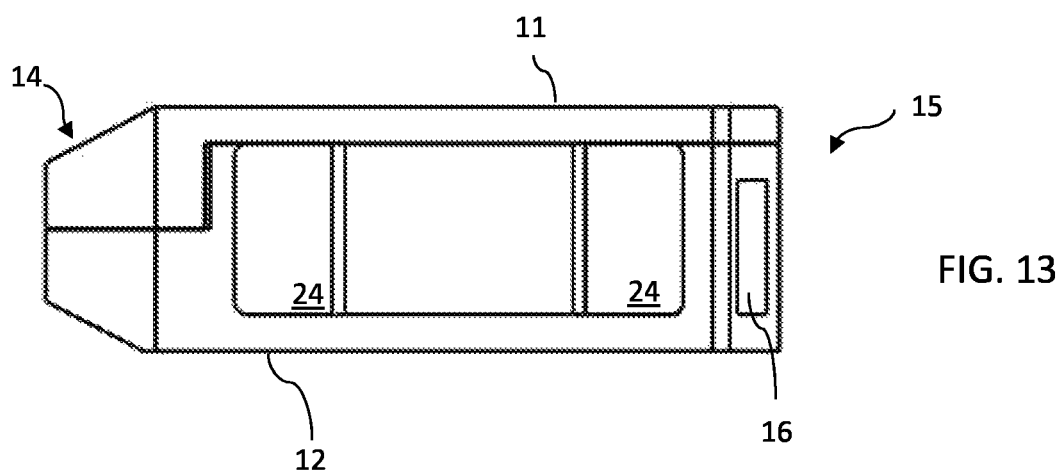
FIG. 13 is a side view of a second embodiment of the spacer of FIG. 12 in an unexpanded position.
Figure 14:
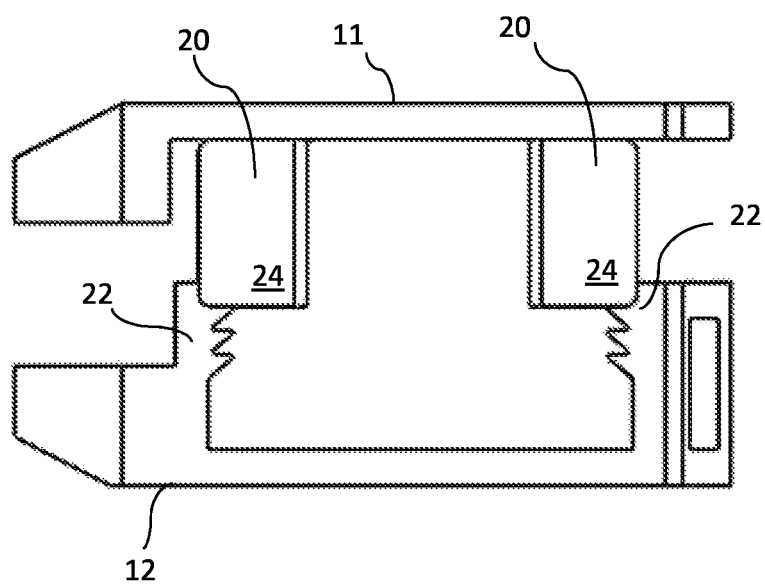
FIG. 14 is a side view of a second embodiment of the spacer of FIG. 12 in an expanded position.
Figure 15:
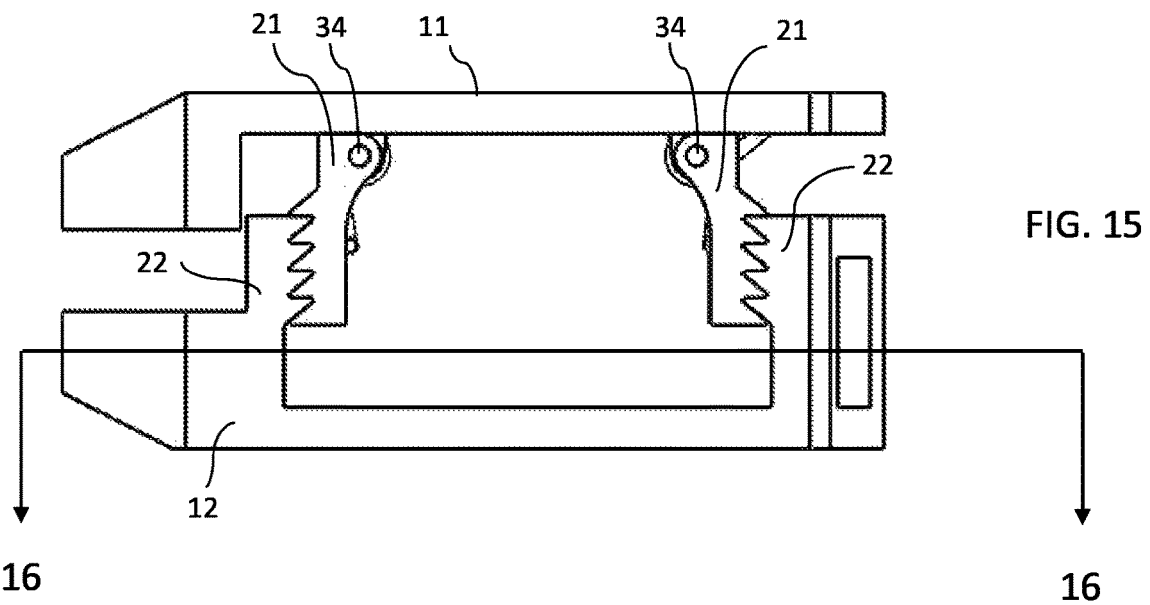
FIG. 15 is a side view of a second embodiment of the spacer of FIG. 12 without the sheaths that cover the ratchet mechanisms, in a partially expanded position.
Figure 16:
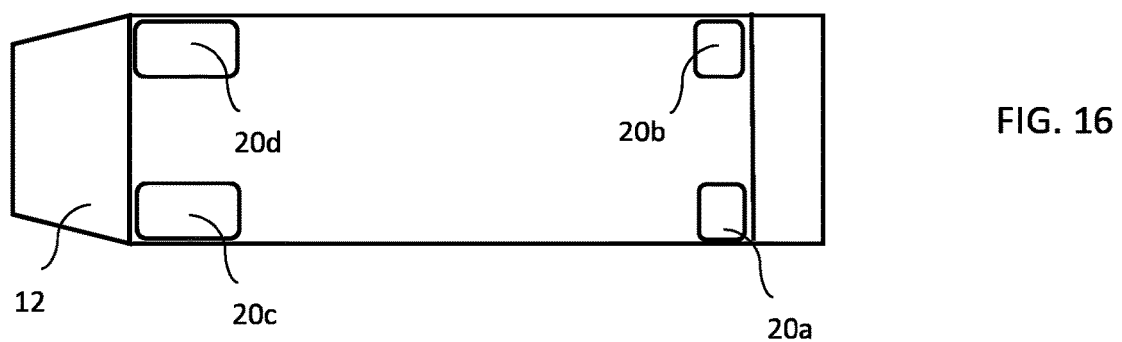
FIG. 16 is a cross-sectional view of the spacer along line 16-16 of FIG. 15.
Figure 17:
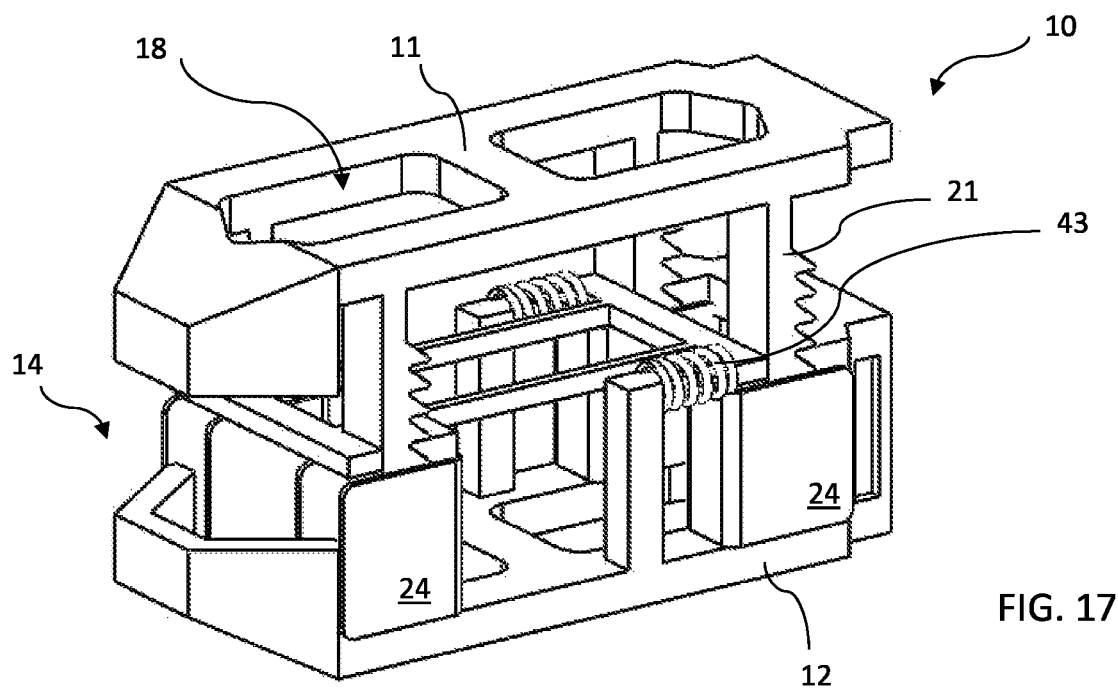
FIG. 17 is a top perspective view of a third embodiment of a spacer in an unexpanded position.
Figure 18:
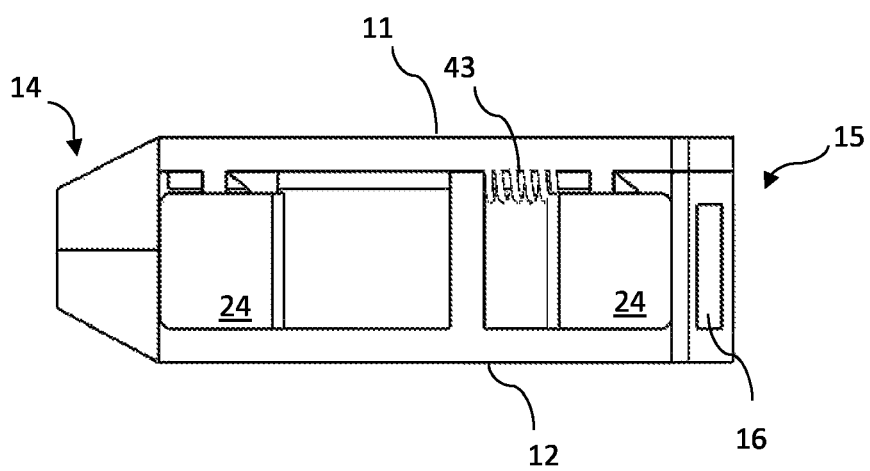
FIG. 18 is a side view of a third embodiment of the spacer of FIG. 17 in an unexpanded position.
Figure 19:
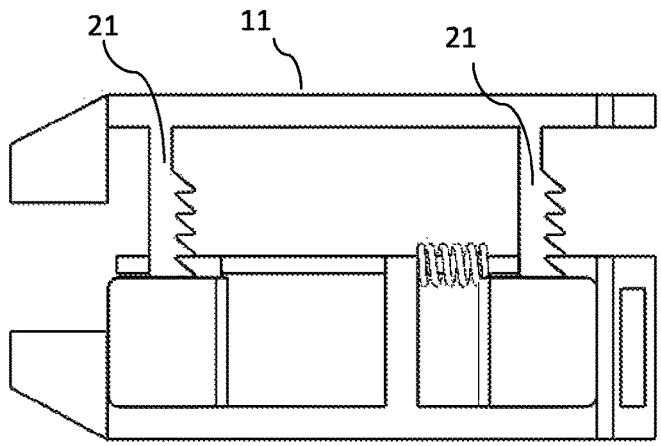
FIG. 19 is a side view of a third embodiment of the spacer of FIG. 17 in an expanded position.
Figure 20:
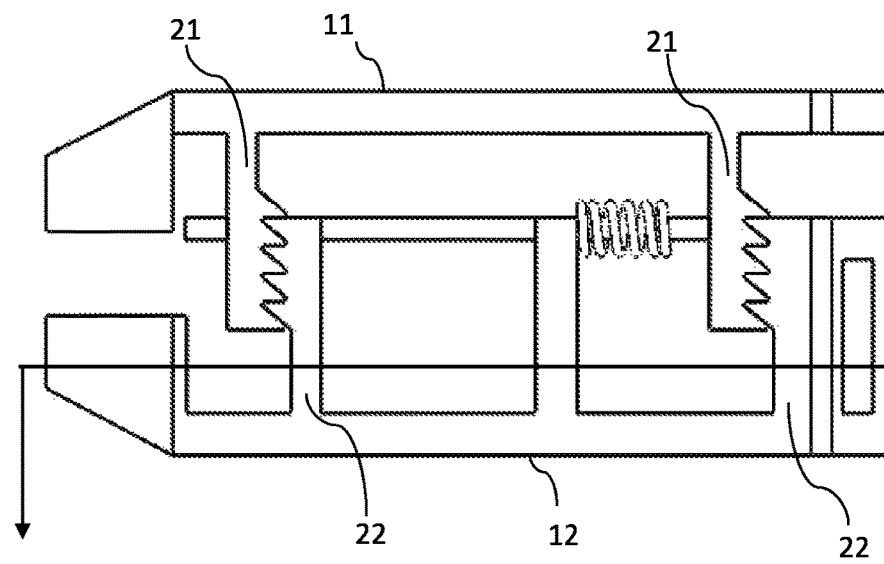
FIG. 20 is a side view of a third embodiment of the spacer of FIG. 17 without the sheaths that cover the ratchet mechanisms, in a partially expanded position.
Figure 21:
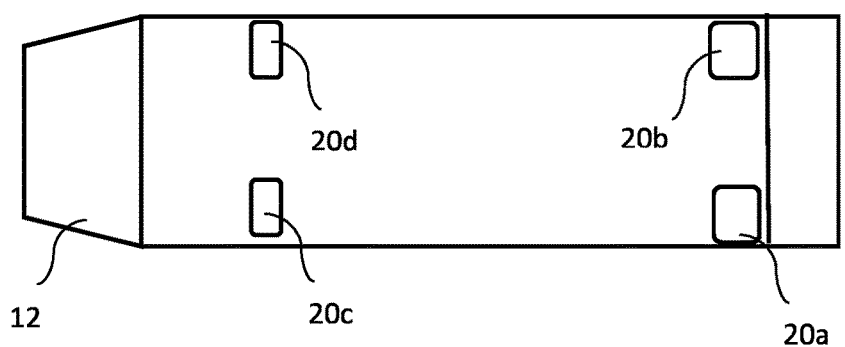
FIG. 21 is a cross-sectional view of the spacer along line 21-21 of FIG. 20.

The spacer is inserted into the patient's body in an unexpanded form using a removable insertion tool 50. FIG. 10 shows a single unexpanded spacer body 10 inserted between two vertebrae 9 which are separated by a distance $d_1$. FIG. 11 shows that single spacer body 10 expanded between the two vertebrae 9, forcing the vertebrae 9 apart a distance $d_2$. The distal end 14 of the spacer body 10 is the leading end when inserting the device between vertebrae and is typically rounded for ease of insertion. The distal end 14 is typically solid so that no debris from the patient's body enters the cavity 17 during insertion, but optionally the distal end 14 may also have cutouts. The other end of the spacer body 10 is an open end 15 to accommodate the removable expansion device and insertion tool.

Figure 5:
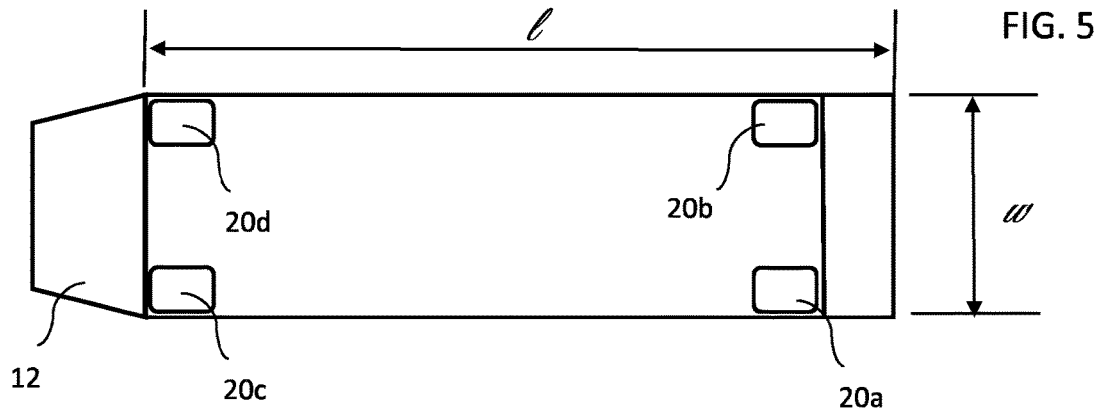
FIG. 5 is a cross-sectional view of the spacer along line 5-5 of FIG. 3.

The spacer is made of a biocompatible material, typically titanium or titanium alloy, and may be made in several sizes. They are typically between 26-30 mm long and 10-11 mm wide. Table 1 shows an exemplary range of sizes, where the height h of the spacer, the width w, and the length l, are shown in FIGS. 1 and 5.

TABLE 1

| Unexpanded Height h (mm) | Fully expanded height h (mm) | Width w (mm) | Length l (mm) |
| --- | --- | --- | --- |
| 7 | 10 | 10 | 28 |
| 8 | 12 | 10 | 28 |
| 9 | 14 | 10 | 28 |
| 10 | 16 | 10 | 28 |

The top and bottom plates 11, 12 are separated and held apart by four ratcheting locking mechanisms, as described in more detail below. The locking mechanisms are positioned to hold the plates parallel to each other when at rest. In some embodiments each locking mechanism is placed at or near a corner of the cage or its periphery. See FIGS. 5, 16 and 21. A person of skill in the art of spacers would recognize that a locking mechanisms "near" the corner or periphery of the cage means the locking mechanisms is not necessarily touching the corner or periphery of the cage. The number and separation of the locking mechanisms optimizes a large open space of the cavity 17 for more bone graft material to be packed into the cage and more exposure to the patient's bone, while being strong enough to withstand compressive forces between the vertebrae. The top, bottom, sides, and the proximal end of the cage has openings 18 where bone graft material is exposed.

Each locking mechanism comprises a stanchion 20. Each stanchion 20a, 20b, 20c, 20d comprises two saw-toothed posts that move relative to one another and cooperate to lock the top plate a desired distance from the bottom plate. One post movable 21 and preferably extends from the top plate 11. The other post is stationary 22 and preferably extends from the bottom plate 22. The posts 21, 22 are forced apart when the top and bottom plates are forced away from each other with the expansion mechanism, due to the cooperative shape of the saw teeth.

Figure 9:
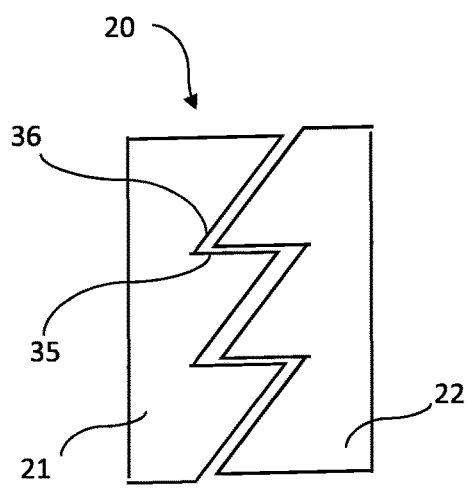
FIG. 9 is a schematic illustration of a post with saw teeth.
Figure 22:
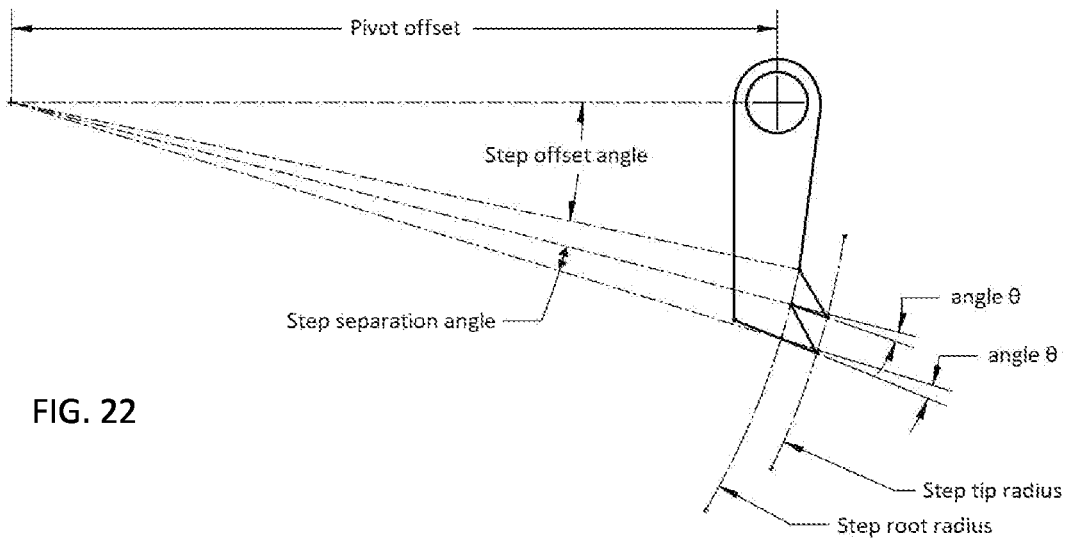
FIG. 22 illustrates effect of saw teeth that are not at 90 degrees to the post.
Figure 23A:
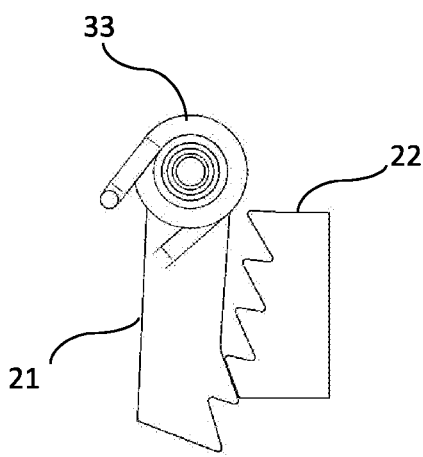
FIGS. 23A-D are side views of the locking mechanism, each with different number of saw-teeth engaged.
Figure 23B:
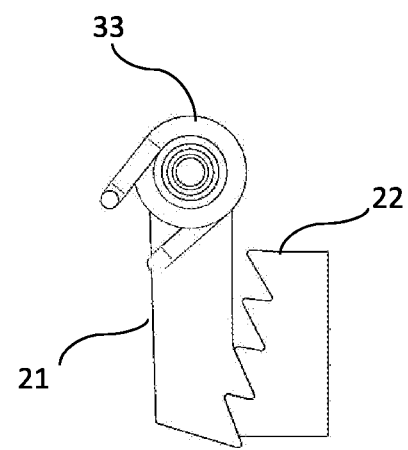
Figure 23C:
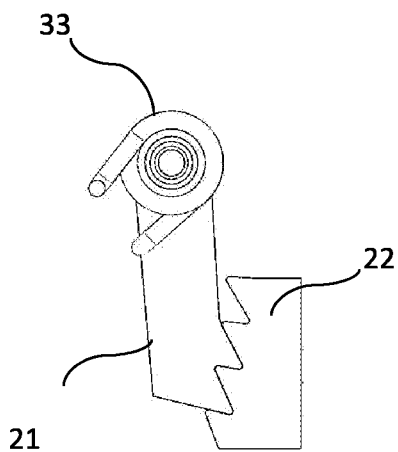
Figure 23D:
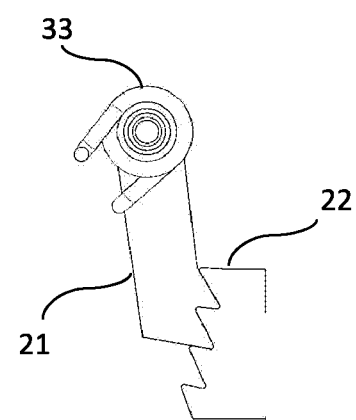
Figure 24:
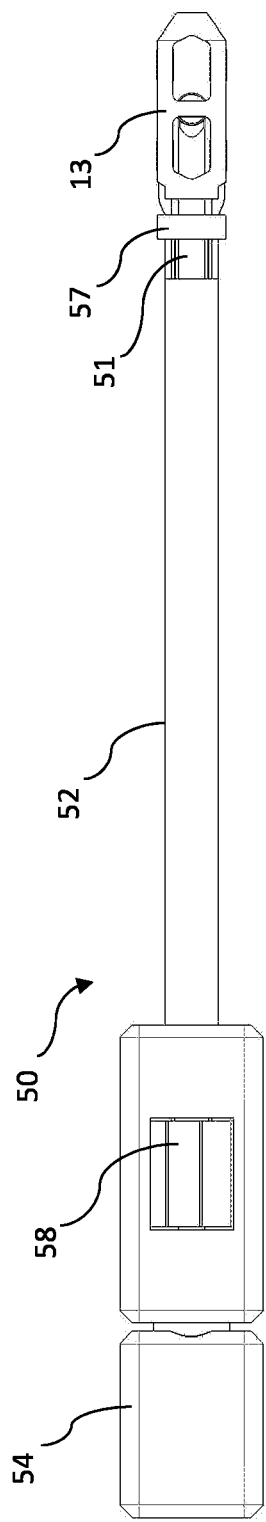
FIG. 24 is a top view of an insertion tool.
Figure 25:
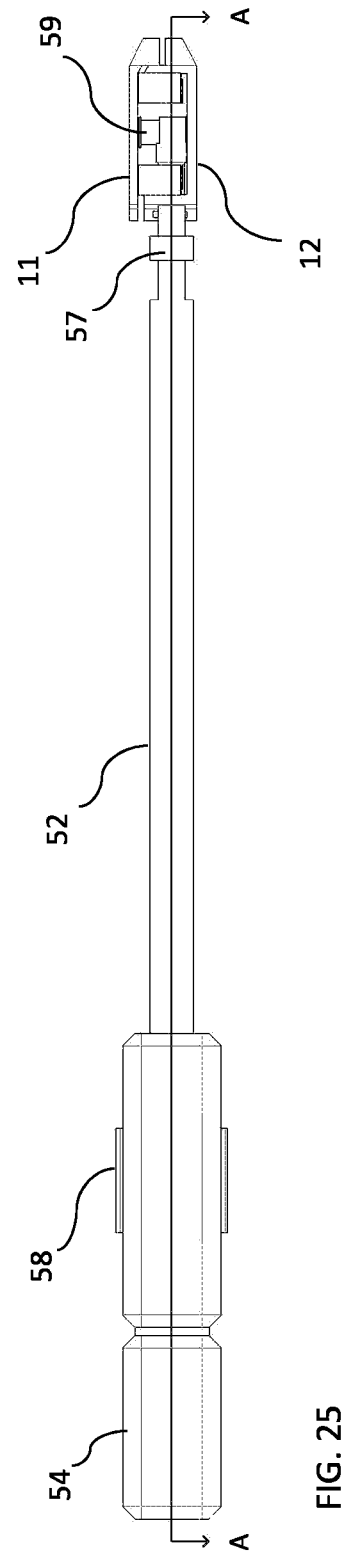
FIG. 25 is a side view of the insertion tool of FIG. 24.
Figure 26:
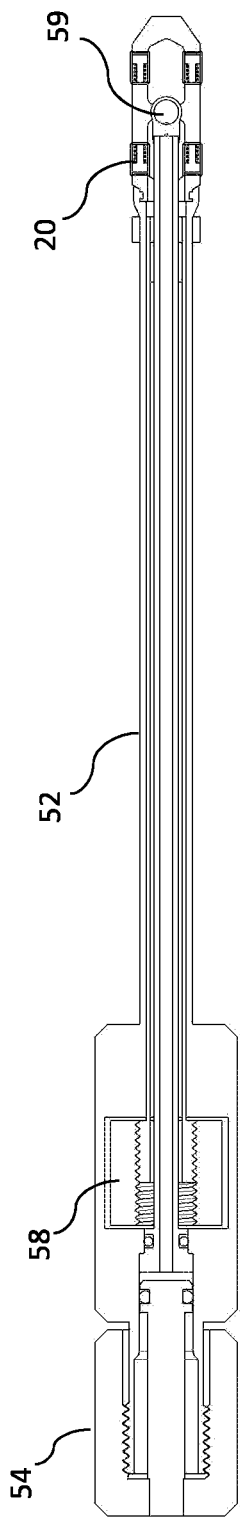
FIG. 26 is top view of the insertion tool of FIG. 25 along line A-A.
Figure 29:
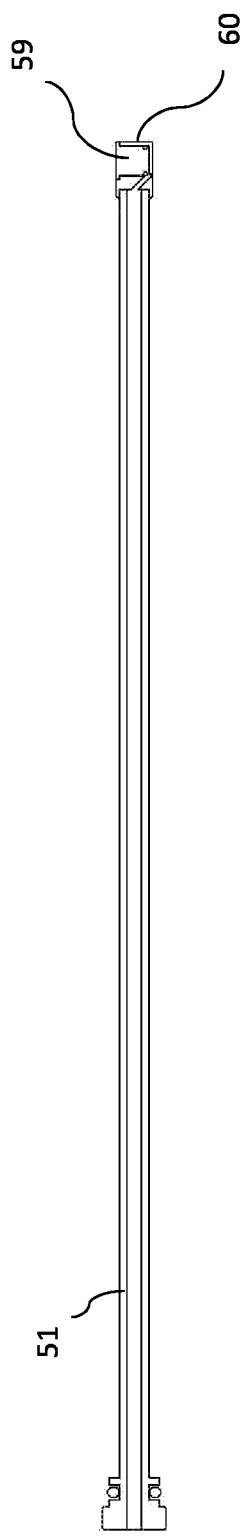
FIG. 29 is a side view of the syringe of FIG. 24 with the piston at rest.
Figure 30:
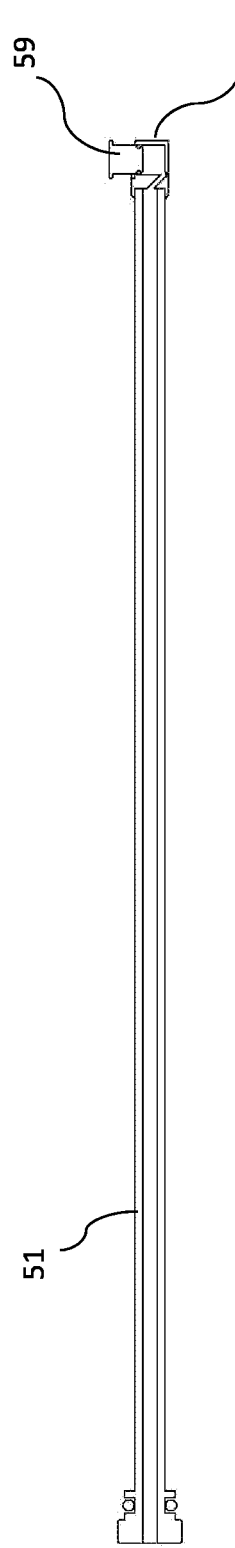
FIG. 30 is a side view of the syringe of FIG. 24 with the piston raised.

Each saw tooth is generally triangular with one side of the triangle extending away from the post at an angle of about 90-106 degrees. This portion of the tooth is referred to herein as the horizontal edge 35. In one embodiment, the horizontal edge is at a right angle to its post, parallel to the top and bottom plates 11, 12. See FIG. 9. In another embodiment, the horizontal edge is greater than 90 degrees to the post, and angle theta shows the difference from perpendicular. See FIGS. 22-23A-D. Angle theta denotes an angular offset from the line between the center-to-root line and root-to-tip line, where the root is the point at which the step attaches to the post. The other edge of the saw tooth is at a complementary angle to its post, referred to herein as the angled edge 36. The teeth of one post intermesh with the teeth of the neighboring post. When the saw teeth are engaged, the horizontal edge 35 of each tooth sits against a horizontal edge 35 of one or more teeth on the opposing post. This holds the top and bottom plates stationary relative to each other, locking the plates to each other. The greater the angle theta of the horizontal edge 35 to the post, the greater the force required to separate the posts 21, 22 from each other. When expanding the cage with horizontal edge at angles more than 90 degrees, the ramp has to be forced open farther than if the horizontal edge is at 90 degrees to get over the lip of the step. Then, the post slides down so that the teeth intermesh. Posts intermeshed with theta angles greater than zero create an interlocking force on the steps which pushes them together and increases the security of the locking mechanism.

The asymmetrical shape of the saw teeth enables the plates to be forced apart incrementally, one saw tooth at a time, in a ratchet-like motion. The posts 21, 22 are forced apart from each other when the top and bottom plates are forced away from each other with the removable expansion mechanism, due to the cooperative shape of the saw teeth. As the top plate is forced away from the bottom plate, as explained in more detail below, the angled edges of the teeth of the top post slide against the angled edges of the teeth of the bottom post, forcing the top post to rotate away from the bottom post in an amount sufficient to release the horizontal edges of the formerly intermeshed teeth.

The height of the saw teeth determines the distance of each increment of separation between the plates: the smaller the tooth height, the finer the degree of separation for each increment. The number of teeth and height of the teeth determine the maximum distance the plates can be separated. At maximum expansion, preferably a minimum of two teeth are engaged on each stanchion.

In one embodiment the horizontal edge 35 of the saw tooth is 2 mm wide and 1.5 mm deep. Assuming two teeth are engaged per stanchion, this provides for a total contact area of 24 mm$^2$ (2 teeth×4 stanchions×1.5 mm wide×2 mm deep). Given a compressive strength of titanium alloy to be 850 MPA, the load to failure is 20,400 N.

Optionally, a sheath 24 surrounds each stanchion or the whole locking mechanism to prevent bone particles and other debris from interfering with the mating of the saw teeth. The sidewall thickness of the sheath 24 is preferably less than 1 mm.

FIGS. 1-5 show a first embodiment of the locking mechanism, a linear ratchet system. For each stanchion 20a, 20b, 20c, 20d, a movable first post 21 cooperates with a stationary second post 22. The posts 21, 22 of each stanchion are biased against each other with one or more springs 23 and the resting position for the posts is interlocked. See FIG. 4. The spring may be a coil spring, a leaf spring, or a spring arm.

To expand the device, the top and bottom plates are forced apart incrementally, one saw tooth at a time, in a ratchet-like motion using a removable insertion tool 50 to operate the expansion mechanism. As the top and bottom plates are forced apart, the springs are compressed and the posts are forced apart and unlocked. The angled edge 36 forces the posts apart until the teeth disengage and raise to the next level. When the top and bottom plates are separated to the desired distance, the spring is allowed to relax, thus forcing the saw teeth of the posts to intermesh again, which locks the top and bottom plates apart at the desired distance.

FIGS. 12-16 show a second embodiment of the locking mechanism, a pivot ratchet system. Again, for each stanchion 20a, 20b, 20c, 20d, a movable first post 21 cooperates with a stationary second post 22, except that in this embodiment the movable first post 21 rotates around an axle 34 that is disposed inside the torsion spring 33 along the spring's longitudinal axis. The posts 21, 22 are biased against each other with two torsions springs 33 disposed at the top plate 11 and the resting position for the posts is interlocked. See FIG. 15.

Again, to expand the device, the top and bottom plates are ratcheted apart incrementally, one saw tooth at a time, using a removable insertion tool to operate the expansion mechanism. As the top and bottom plates are forced apart, the torsion springs are compressed and the posts are forced apart and unlocked. When the top and bottom plates are separated to the desired distance, the torsion springs are allowed to relax, thus forcing the saw teeth of the posts to intermesh again, which locks the top and bottom plates apart at the desired distance.

FIGS. 17-21 show a third embodiment of the locking mechanism. Again, for each stanchion 20a, 20b, 20c, 20d, a movable first post 21 cooperates with a stationary second post 22. The posts 41, 42 of each stanchion are biased against each other with two coil springs 43 disposed on the bottom plate 12. The resting position for the posts is interlocked.

Again, the top and bottom plates are ratcheted apart incrementally, one saw tooth at a time to expand the spacer, using a removable insertion tool to operate the expansion mechanism. As the top and bottom plates are forced apart, the springs are compressed and the posts are forced apart and unlocked. When the top and bottom plates are separated to the desired distance, the coil springs are allowed to relax, thus forcing the saw teeth of the posts to intermesh again, which locks the top and bottom plates apart at the desired distance.

The insertion tool 50 has clamping arms 55 and 56 that mate with clamping slots 16 on the proximal end 15 of the spacer body. See FIGS. 24-30. The ends of the clamping arms are tabs that fit in the clamp slots 16 on the proximal end of the spacer body so that the insertion tool can securely hold on to the spacer body during insertion and release it once inserted. The clamp arm tabs are inserted into the clamp slots 16, and the tabs are closed toward each other by moving the clamp collar 57 toward the end of the clamp arms. The clamp collar 57 is moved over the clamp arms by rotating a threaded cylinder 58. Rotation of the cylinder 58 in a first direction moves the collar 57 toward the spacer body, tightening the tabs in the clamp slots 16 of the spacer body. Rotation of the cylinder 58 in the reverse direction moves the collar 57 away from the cage, loosening the tabs from the slots of the cage.

Once the cage is clamped to the insertion tool, the expansion mechanism and the spacer are implanted into the patient simultaneously using the mated insertion tool 50, which also operates the expansion mechanism. The spacer 10 is inserted into the patient's body in an unexpanded form and rests on the lower vertebra of the two being separated or on the bottom plate of the spacer. The distal end 14 of the spacer 10 is the leading end when inserting the spacer between vertebrae and is typically closed and rounded for ease of insertion. The proximal end 15 of the spacer 10 is open to accommodate the expansion mechanism. The cage is moveable between a collapsed configuration and an expanded configuration using the removable expansion mechanism.

Figure 31:
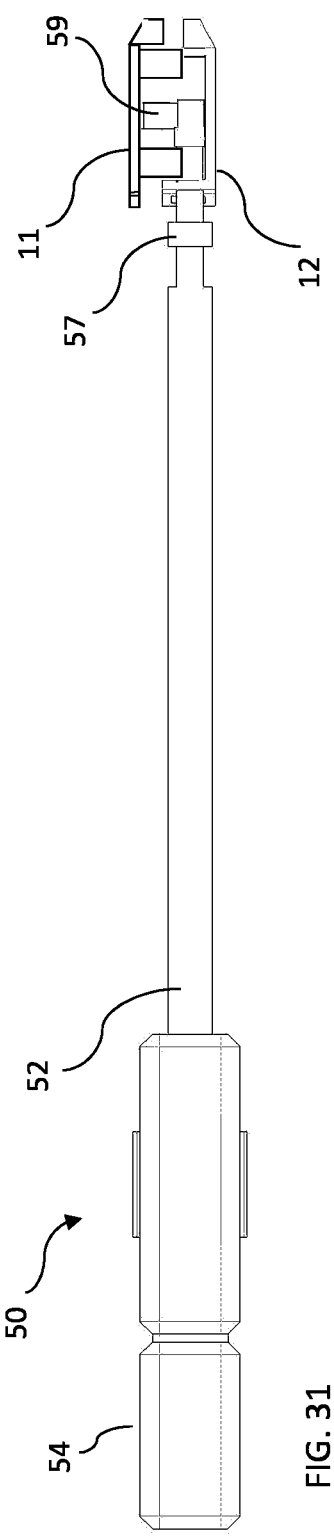
FIG. 31 is a side view of the insertion tool with the syringe extending into the spacer and the piston raised.

The inserter tool 50 houses the expansion mechanism, which may be a hydraulic piston, scissor jack, SpineJack®, cam, balloon or other device. A hydraulic piston is used herein as an example of the removable expansion mechanism. See FIGS. 24-35. The inserter tool 50 comprises the clamping arms 55, 56 at the distal end of a hollow shaft 52. Inside the hollow shaft is a hydraulic expansion mechanism comprising a syringe 51 with a piston 59 movable in a piston collar 60 at the end of the syringe. The syringe 51 is closed at the piston end. Once the cage is inserted into the patient with the insertion tool 50, the syringe 51 is filled with fluid, typically water or air, which forces the piston 59 to move up against the top plate 11 and push it away from the bottom plate. The hydraulic pressure is increased until the top plate 11 and bottom plate 12 are forced apart a desired distance. See FIG. 31. Once the plates 11, 12 are separated by the desired distance, the hydraulic pressure in the syringe 51 is reduced so that the piston 59 drops back into the piston collar 60. Once the plates are separated the desired distance, the expansion mechanism is withdrawn from the spacer body as the insertion tool is withdrawn from the patient. Then bone graft material is packed in and around the spacer to provide a scaffolding so that new bone can be formed. The bone graft material may be cancellous or cortical bone, or both, and is preferably autograft or allograft tissue.

While there has been illustrated and described what is at present considered to be the preferred embodiments of the present invention, it will be understood by those skilled in the art that various changes and modifications may be made and equivalents may be substituted for elements thereof without departing from the true scope of the invention. Therefore, it is intended that this invention not be limited to the particular embodiments disclosed, but that the invention will include all embodiments falling within the scope of the appended claims.

The invention claimed is:

1. An expandable intervertebral spacer system, the spacer system comprising:
   a) a top plate having a top periphery and a top surface within the top periphery and a bottom plate having a bottom periphery and a bottom surface within the bottom periphery, wherein the top plate and bottom plate form a cage surrounding a cavity, wherein the cage has a proximal end and a distal end;
   b) four locking mechanisms separating the top plate and bottom plate;
   c) a stanchion comprising a movable post having saw teeth and a stationary post having saw teeth; and
   d) a spring configured to bias the movable post against the stationary post, such that the movable post and stationary post cooperate to lock the top plate and bottom plate apart a desired distance.

2. The system according to claim 1 wherein each spring is configured to exert a linear force on the respective movable post to lock the top plate and bottom plate apart a desired distance.

3. The system according to claim 1 wherein each spring is configured to exert a rotary force on the respective movable post to lock the top plate and bottom plate apart a desired distance.

4. The system according to claim 1 wherein each locking mechanism is disposed at or near a corner of the cage.

5. The system according to claim 1 wherein the top surface of the top plate and the bottom surface of the bottom plate have cutouts.

6. The system according to claim 1 further comprising a removable insertion tool insertable into the cavity from the proximal end of the cage, wherein the insertion tool is configured to operate a removable expansion mechanism which forces the top plate and bottom plate apart.

7. The system according to claim 6 wherein the removable expansion mechanism is a scissor jack, hydraulic piston, cam, or balloon.

8. The system according to claim 1 wherein the cage is moveable between a collapsed configuration and an expanded configuration, and wherein in the expanded configuration the top plate and bottom plate are parallel.

9. An expandable intervertebral spacer system, the spacer system comprising:
   a) a top plate having a top periphery and a top surface within the top periphery and a bottom plate having a bottom periphery and a bottom surface within the bottom periphery, wherein the top plate and bottom plate form a cage surrounding a cavity, wherein the cage has a proximal end and a distal end;
   b) four stanchions separating the top plate and bottom plate wherein each stanchion comprises a movable post having saw teeth and a stationary post having saw teeth, wherein;
      i) each of the movable post and stationary post saw teeth has a horizontal edge;
      ii) the horizontal edge of the saw teeth on the stationary post are at an angle greater than 90 degrees to the stationary post; and
      iii) the horizontal edge of the saw teeth on the movable post are at an angle to the movable post that is complementary angle to the saw teeth on the stationary post; and
   c) four springs, each configured to bias one of the movable posts against the respective stationary post, such that each movable post and respective stationary post cooperate to lock the top plate and bottom plate apart a desired distance.

10. The system according to claim 9 wherein each spring is configured to exert a linear force on the respective movable post to lock the top plate and bottom plate apart a desired distance.

11. The system according to claim 9 wherein each spring is configured to exert a rotary force on the respective movable post to lock the top plate and bottom plate apart a desired distance.

12. The system according to claim 9 wherein the top surface of the top plate and the bottom surface of the bottom plate have cutouts.

13. The system according to claim 9 further comprising a removable insertion tool insertable into the cavity from the proximal end of the cage, wherein the insertion tool is configured to operate a removable expansion mechanism which forces the top plate and bottom plate apart.

14. The system according to claim 13 wherein the removable expansion mechanism is a scissor jack, hydraulic piston, cam, or balloon.

15. The system according to claim 9 wherein the cage is moveable between a collapsed configuration and an expanded configuration, and wherein in the expanded configuration the top plate and bottom plate are parallel.

16. An expandable intervertebral spacer system, the spacer system comprising:
   a) a top plate and a bottom plate forming a cage surrounding a cavity, wherein the cage has a proximal end and a distal end;
   b) four locking mechanisms separating the top plate and bottom plate;
   c) a stanchion comprising a movable post having saw teeth and a stationary post having saw teeth; and
   d) a spring configured to bias the movable post against the stationary post, such that the movable post and stationary post cooperate to lock the top plate and bottom plate apart a desired distance.

17. The system according to claim 16 wherein each spring is configured to exert a linear force on the respective movable post to lock the top plate and bottom plate apart a desired distance.

18. The system according to claim 16 wherein each spring is configured to exert a rotary force on the respective movable post to lock the top plate and bottom plate apart a desired distance.

19. The system according to claim 16 wherein each locking mechanism is disposed at or near a corner of the cage.

20. The system according to claim 16 wherein the top plate and the bottom plate have cutouts.

21. The system according to claim 16 further comprising a removable insertion tool insertable into the cavity from the proximal end of the cage, wherein the insertion tool is configured to operate a removable expansion mechanism which forces the top plate and bottom plate apart.

22. The system according to claim 21 wherein the removable expansion mechanism is a scissor jack, hydraulic piston, cam, or balloon.

23. The system according to claim 16 wherein the cage is moveable between a collapsed configuration and an expanded configuration, and wherein in the expanded configuration the top plate and bottom plate are parallel.

24. An expandable intervertebral spacer system, the spacer system comprising:
   a) a top plate and a bottom plate forming a cage surrounding a cavity, wherein the cage has a proximal end and a distal end;
   b) four stanchions separating the top plate and bottom plate wherein each stanchion comprises a movable post having saw teeth and a stationary post having saw teeth, wherein;
      i) each of the movable post and stationary post saw teeth has a horizontal edge;
      ii) the horizontal edge of the saw teeth on the stationary post are at an angle greater than 90 degrees to the stationary post; and
      iii) the horizontal edge of the saw teeth on the movable post are at an angle to the movable post that is complementary angle to the saw teeth on the stationary post; and
   c) four springs, each configured to bias one of the movable posts against the respective stationary post, such that each movable post and respective stationary post cooperate to lock the top plate and bottom plate apart a desired distance.

25. The system according to claim 24 wherein each spring is configured to exert a linear force on the respective movable post to lock the top plate and bottom plate apart a desired distance.

26. The system according to claim 24 wherein each spring is configured to exert a rotary force on the respective movable post to lock the top plate and bottom plate apart a desired distance.

27. The system according to claim 24 wherein the top plate and the bottom plate have cutouts.

28. The system according to claim 24 further comprising a removable insertion tool insertable into the cavity from the proximal end of the cage, wherein the insertion tool is configured to operate a removable expansion mechanism which forces the top plate and bottom plate apart.

29. The system according to claim 28 wherein the removable expansion mechanism is a scissor jack, hydraulic piston, cam, or balloon.

30. The system according to claim 24 wherein the cage is moveable between a collapsed configuration and an expanded configuration, and wherein in the expanded configuration the top plate and bottom plate are parallel.

* * * * *